(12) United States Patent
Martin et al.

(10) Patent No.: US 7,390,819 B2
(45) Date of Patent: Jun. 24, 2008

(54) IMIDAZO[4,5-B]QUINOLINE-DERIVATIVES AND THEIR USE AS NO-SYNTHASE INHIBITORS

(75) Inventors: Thomas Martin, Constance (DE); Wolf-Ruediger Ulrich, Constance (DE)

(73) Assignee: Altana Pharma AG, Constance (DE)

( * ) Notice: Subject to any disclaimer, the term of this patent is extended or adjusted under 35 U.S.C. 154(b) by 223 days.

(21) Appl. No.: 10/546,198

(22) PCT Filed: Feb. 24, 2004

(86) PCT No.: PCT/EP2004/050201

§ 371 (c)(1),
(2), (4) Date: Aug. 18, 2005

(87) PCT Pub. No.: WO2004/076451

PCT Pub. Date: Sep. 10, 2004

(65) Prior Publication Data

US 2006/0160839 A1    Jul. 20, 2006

(30) Foreign Application Priority Data

Feb. 25, 2003    (EP) .................................. 03004102

(51) Int. Cl.
*A61K 31/437* (2006.01)
*C07D 471/04* (2006.01)

(52) U.S. Cl. .......................................... 514/293; 546/84

(58) Field of Classification Search .................. 546/84; 514/293
See application file for complete search history.

(56) References Cited

U.S. PATENT DOCUMENTS 4,045,564 A    8/1977    Berntsson et al.
4,603,139 A    7/1986    King

FOREIGN PATENT DOCUMENTS

| DE | 25 04 252 C2 | 8/1975 |
| EP | 0 125 756 A2 | 11/1984 |
| WO | 97/43288 A1 | 11/1997 |

OTHER PUBLICATIONS

Dorwald F. A. Side Reactions in Organic Synthesis, 2005, Wiley: VCH, Weinheim p. IX of Preface.*

* cited by examiner

*Primary Examiner*—Rita J Desai
(74) *Attorney, Agent, or Firm*—The Nath Law Group; Joshua B. Goldberg; Sheldon N. McGee

(57) ABSTRACT

The compounds of formula I

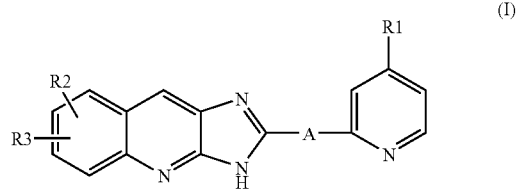

in which R1, R2, R3 and A have the meanings as given in the description are novel effective INOS inhibitors.

6 Claims, No Drawings

IMIDAZO[4,5-B]QUINOLINE-DERIVATIVES AND THEIR USE AS NO-SYNTHASE INHIBITORS

FIELD OF APPLICATION OF THE INVENTION

The invention relates to novel imidazo[4,5b]quinoline derivatives, which are used in the pharmaceutical industry for the production of pharmaceutical compositions.

KNOWN TECHNICAL BACKGROUND

In the German Patent Application DE 2504252 and in the European Patent Application EP 0125758 3H-imidazo[4,5-b]pyridine derivatives with anti-ulcer activity are described.

DESCRIPTION OF THE INVENTION

It has now been found that the novel imidazo[4,5-b]quinoline derivatives, which are described in greater details below, have surprising, unanticipated and particularly advantageous properties.

The invention thus relates to compounds of formula I

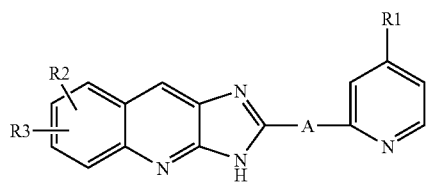

in which
R1 is 1-4C-alkoxy;
A is 1-4C-alkylene;
R2 is hydrogen; halogen; hydroxyl; nitro; amino; 1-7C-alkyl; trifluoromethyl; 3-7C-cycloalkyl; 3-7C-cycloalkyl-1-4C-alkyl; 1-4C-alkoxy; completely or predominantly fluorine-substituted 1-4C-alkoxy; 1-4C-alkoxy-1-4C-alkyl; 1-4C-alkoxy-1-4C-alkoxy; mono- or di-1-4C-alkylaminocarbonyl; mono- or di-1-4C-alkylaminosulfonyl; 1-4C-alkylcarbonylamino; 1-4C-alkylsulfonylamino; phenyl; phenyl-1-4C-alkyl; phenyl-1-4C-alkoxy; R21- and/or R22-substituted phenyl; phenyl-1-4C-alkyl wherein the phenyl moiety is substituted by R23; Het; R24-substituted Het; Het-1-4C-alkyl; Het-1-4C-alkyl wherein the Het moiety is substituted by R25; in which
R21 is cyano; halogen; carboxyl; 1-4C-alkyl; 1-4C-alkoxy; hydroxy-1-4C-alkyl; 1-4C-alkoxy-1-4C-alkyl; 3-7C-cycloalkoxy, 3-7C-cycloalkylmethoxy; completely or predominantly fluorine-substituted 1-4C-alkoxy; aminocarbonyl; mono- or di-1-4C-alkylaminocarbonyl; 1-4C-alkylcarbonylamino; 1-4C-alkoxycarbonyl; aminosulfonyl; mono-or di-1-4C-alkylaminosulfonyl; amino; trifluoromethyl; hydroxyl; phenylsulfonylamino; or phenyl-1-4C-alkoxy;
R22 is halogen; 1-4C-alkyl; or 1-4C-alkoxy;
or wherein R21 and R22 together are a 1-2C-alkylenedioxy group;
R23 is halogen; 1-4C-alkyl; or 1-4C-alkoxy;
Het represents a mono- or bicyclic single or fused 5 to 10-membered heteroaryl radical containing one to three heteroatoms, each of which is selected from a group consisting of nitrogen, oxygen and sulfur;
R24 is halogen; 1-4C-alkyl; or 1-4C-alkoxy;
R25 is halogen; 1-4C-alkyl; or 1-4C-alkoxy;
R3 is hydrogen; halogen; 1-4C-alkyl; or 1-4C-alkoxy;
the salts; the N-oxides; and the salts of the N-oxides of these compounds.

1-4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

1-4C-Alkylene is a straight chain alkylene radical having 1 to 4 carbon atoms. Examples which may be mentioned in this context are the methylene (—CH$_2$—), ethylene (—CH$_2$—CH$_2$—), trimethylene (—CH$_2$—CH$_2$—CH$_2$—) and the tetramethylene (—CH$_2$—CH$_2$—CH$_2$—CH$_2$—) radical.

1-4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, rec-butoxy, tertbutoxy, propoxy, iso-propoxy, ethoxy and methoxy radicals.

1-2C-Alkylenedioxy represents, for example, the methylenedioxy [—O—CH$_2$—O—] and the ethylenedioxy [—O—CH$_2$—CH$_2$—O—] radicals.

3-7C-Cycloalkyl stands for cyclopropyl, cyclobutyl, cyclopentyl, cyclohexyl and cycloheptyl, of which cyclopropyl, cyclobutyl and cyclopentyl are preferred.

3-7C-Cycloalkoxy stands for cyclopropoxy, cyclobutoxy, cyclopentoxy, cyclohexoxy and cycloheptoxy, of which cyclopropoxy, cyclobutoxy and cyclopentoxy are preferred.

3-7C-Cycloalkyl stands for one of the abovementioned 1-4C-alkyl radicals, which is substituted by one of the abovementioned 3-7C-cycloalkyl radicals. Examples which may be mentioned are the cyclopropylmethyl, the cyclohexylmethyl and the cyclohexylethyl radicals.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Halogen within the meaning of the present invention is bromine, chlorine or fluorine.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-fluoroethoxy, the trifluoromethoxy and the difluoromethoxy radical, of which the difluoromethoxy radical is preferred. "Predominantly" in this connection means that more than half of the hydrogen atoms of the 1-4C-alkoxy radical are replaced by fluorine atoms.

1-4C-Alkoxy-1-4C-alkoxy stands for one of the abovementioned 1-4C-alkoxy radicals which is substituted by the same or another of the abovementioned 1-4C-alkoxy radicals. Examples which may be mentioned are the 2-(methoxy)ethoxy (—O—CH$_2$—CH$_2$—O—CH$_3$) and the 2-(ethoxy)ethoxy radical (—O—CH$_2$—CH$_2$—O—CH$_2$—CH$_3$).

1-4C-Alkoxy-1-4C-alkyl stands for one of the abovementioned 1-4C-alkyl radicals which is substituted by one of the abovementioned 1-4C-alkoxy radicals. Examples which may be mentioned are the 2-methoxyethyl, the 2-ethoxyethyl and the 3-methoxypropyl radical.

Hydroxy-1-4C-alkyl stands for one of the abovementioned 1-4C-alkyl radicals which is substituted by a hydroxy group. Examples which may be mentioned em the 1-hydroxymethyl, the 2-hydroxyethyl and the 3-hydroxypropyl radical.

Mono- or Di-1-4C-alkylamino radicals contain in addition to the nitrogen atom, one or two of the abovementioned 1-4C-alkyl radicals. Preferred are the di-1-4C-alkylamino radicals, especially the dimethylamino, the diethylamino and the diisopropylamino radical.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

Mono-or Di-1-4C-alkylaminosulfonyl stands for a sulfonyl group to which one of the abovementioned mono- or di-1-4C-alkylamino radicals is bonded. Examples which may be mentioned are the methylaminosulfonyl, the dimethylaminosulfonyl and the ethylaminosulfonyl radical. An 1-4C-Alkylcarbonylamino radical is, for example, the propionylamino [$C_3H_7C(O)NH—$] and the acetylamino radical [$CH_3C(O)NH—$].

An 1-4C-Alkylsulfonylamino radical is, for example, the propylsulfonylamino [$C_3H_7S(O)_2NH—$] and the methylsulfonylamino radical [$CH_3S(O)_2NH—$].

1-4C-Alkoxycarbonyl is a carbonyl group to which one of the abovementioned 1-4C-alkoxy radicals is bonded. Examples are the methoxycarbonyl [$CH_3O—C(O)—$] and the ethoxycarbonyl [$CH_3CH_2O—C(O)—$] radical.

Phenyl-1-4C-alkoxy stands for one of the abovementioned 1-4C-alkoxy radicals, which is substituted by the phenyl radical. Examples which may be mentioned are the benzyloxy and the phenethoxy radical.

Phenyl-1-4C-alkyl stands for one of the abovementioned 1-4C-alkyl radicals, which is substituted by a phenyl radical. Examples which may be mentioned are the phenylethyl and the benzyl radical.

N-oxide denotes the N-oxide on the pyridine which is substituted by R1.

Het represents a mono- or bicyclic single or fused 5 to 10-membered heteroaryl radical containing one to three heteroatoms, each of which is selected from a group consisting of nitrogen, oxygen and sulfur, and includes, for example, without being restricted to furanyl, thiophenyl, pyrrolyl, oxazolyl, isoxazolyl, thiazolyl, isothiazolyl, imidazolyl, pyrazolyl, triazolyl, thiadiazolyl, oxadiazolyl, pyridinyl, pyrimidinyl, pyrazinyl, pyridazinyl, benzo-fused analogues thereof, such as, for example, benzofuranyl, indolyl, benzothiophenyl, benzimidazolyl, benzothiazolyl, benzoxazolyl or quinolinyl, or imidazopyridinyl or imidazopyridazinyl. Preferably, the bicyclic fused 9- or 10 membered heteroaryl radicals, such as, for example, the benzo-fused analogues (e.g. benzofuranyl, indolyl, benzothiophenyl, benzimidazolyl, benzothiazolyl, benzoxazolyl or quinolinyl) or imidazopyridinyl or imidazopyridazinyl, are to be mentioned, whereby said benzo-fused analogues are particularly preferred.

Het-1-4C-alkyl stands for one of the abovementioned 1-4C-alkyl radicals, which is substituted by one of the abovementioned Het radicals. Examples which may be mentioned are the Het-ethyl and the Het-methyl radical, particularly, the pyridylethyl and the pyridylmethyl radical.

The person skilled in the art is aware on account of his/her expert knowledge that, with regard to the R24-substituted or R25-substituted Het radical, certain combinations of the substituents R24 or R25 with the Het radical would lead to chemically less stable compounds. This can apply, for example, to certain 5-membered Het radicals which are substituted with an electron rich radical, such as, for example, the 1-4C-alkoxy radical might be. With regard to the R24-substituted or R25-substituted Het radical, those compounds according to the invention, in which the combination of the substituent R24 or R25 with the Het radical does not lead to chemically less stable compounds, are therefore preferred. If Het represents a R24-substituted or R25-substituted benzofused Het radical, the Het radical is preferably substituted on the benzo ring.

Exemplary unsubstituted heteroaryl radicals Het which may be mentioned are furan-2-yl, furan-3-yl, thiophen-2-yl, thiophenyl, 1H-pyrrol-2-yl, 1H-pyrrolyl, pyrazol-3-yl, pyrazol-4-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, isoxazol-4-yl, isoxazol-5-yl, isothiazol-3-yl, isothiazol-4-yl, isothiazol-5-yl, [1,2,3]thiadiazol-4-yl, [1,2,3]thiadiazol-5-yl, pyridin-2-yl, pyridin-3-yl, pyridin-4-yl, pyrimidin-4-yl, pyrimidin-5-yl, pyrimidin-2-yl, pyridazin-4-yl, pyridazin-3-yl, pyrazin-2-yl, indol-2-yl, indol-3-yl, benzofuran-2-yl, benzofuran-3-yl, benzothiophen-2-yl and benzothiophen-3-yl.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to experts knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of formula I to be emphasized are those in which

R1 is 1-4C-alkoxy;
A is 1-4C-alkylene;
R2 is hydrogen; halogen; 1-7C-alkyl; trifluoromethyl; 1-4C-alkoxy; completely or predominantly fluorine-substituted 1-2C-alkoxy, phenyl; R21- and/or R22-substituted phenyl; or Het; wherein
R21 is 1-4C-alkyl; 1-4C-alkoxy; hydroxy-1-4C-alkyl; 1-2C-alkoxy-1-2C-alkyl; completely or predominantly fluorine-substituted 1-2C-alkoxy;
R22 is 1-4C-alkoxy;
Het represents a bicyclic fused 9- or 10-membered heteroaryl radical containing one to three heteroatoms, each of which is selected from a group consisting of nitrogen, oxygen and sulfur;
R3 is hydrogen;

the salts; the N-oxides; and the salts of the N-oxides of these compounds.

Preferred compounds of formula I are those wherein either
R1 is methoxy;
A is ethylene;
R2 is hydrogen; halogen; 1-4C-alkyl; 1-4C-alkoxy; R21- and/or R22-substituted phenyl; or Het; wherein
R21 is 1-4C-alkoxy;
R22 is 1-4C-alkoxy;
Het is benzofuranyl; or benzothiophenyl;
R3 is hydrogen;

or
R1 is methoxy;
A is ethylene;
R2 is hydrogen; halogen; 1-4C-alkyl; 1-4C-alkoxy; R21-substituted phenyl; or Het; wherein
R21 is hydroxy-1-4C-alkyl;
Het is benzofuranyl; or benzothiophenyl;
R3 is hydrogen;

the salts; the N-oxides; and the salts of the N-oxides of these compounds.

Examples of imidazo[4,5-b]quinoline compounds within the scope of this invention are:
2-[2-(4-methoxypyridin-2-yl)ethyl]-3H-imidazo[4,5-b]quinoline,
2-[2-(4-methoxypyridin-2-yl)ethyl]-7-methyl-3H-imidazo[4,5-b]quinoline,
2-[2-(4-methoxypyridin-2-yl)ethyl]-5-methyl-3H-imidazo[4,5-b]quinoline.
7-methoxy-2-[2-(4-methoxypyridin-2-yl)ethyl]-3H-imidazo[4,5b]quinoline,
7-bromo-2-[2-(4-methoxypyridin-2-yl)ethyl]-3H-imidazo[4,5-b]quinoline,
7-(4-hyroxymethylphenyl)-2-[2-(4-methoxypyridin-2-yl)ethyl]-3H-imidazo[4,5-b]quinoline,
7-benzofuran-2-yl-2-[2-4-methoxypyridin-2-yl)ethyl]-3H-imidazo-[4,5-b]quinoline,
7-(3,4-dimethoxyphenyl)-2-[2-4-methoxypyridin-2-yl)ethyl]-3H-imidazo[4,5-b]quinoline.

the salts, the N-oxides and the salts of the N-oxides of these compounds.

A special embodiment of the compounds of the present invention include those compounds of formula I in which R1 is methoxy.

Another special embodiment of the compounds of the present invention include those compounds of formula I in which A is ethylene.

A further special embodiment of the compounds of the present invention include those compounds of formula I in which R3 is hydrogen.

Still a further special embodiment of the compounds of the present invention include those compounds of formula I in which R1 is methoxy and A is ethylene.

Still a further special embodiment of the compounds of the present invention include those compounds of formula I in which R1 is methoxy, R3 is hydrogen and A is ethylene.

The compounds of formula I according to the invention can, for example, be prepared as described in the following examples according to the following reaction schemes or as known to one of ordinary skill in the art, e.g. in a manner similar or analogous to art-known processes.

In reaction scheme 1 the synthesis of compounds of formula I, in which R1 is alkoxy, A is ethylene and R2 and R3 independently of one another have the meanings indicated above, is described, whereby each reaction step can be carried out as specified by way of example in the following examples or analogously or similarly thereto or as known to the person skilled in the art.

In a first reaction step the nitro group of the commercially available 4-nitro-2-picoline-N-oxide is exchanged by a 1-4C-alkoxy group. The resulting 4-(1-4C)-alkoxy-2-picoline-N-oxide (compound of formula VIII) is then converted via a rearrangement into a compound of formula VI, which is oxidized to give 4-(1-4C)alkoxy-pyridin-2-carbaldehyde (compound of formula VI).

The carbon chain in 2-position of the compounds of formula VI is lengthened, for example, by a condensation (with a malonic acid derivative) and a subsequent hydrogenation reaction. Alternatively, the carbon chain can be lengthened using a Wittig reaction followed by a hydrogenation reaction.

In the last step the methyl 3-(4-(1-4C)-alkoxypyridin-2-yl) propionate (compound of formula IV) or the corresponding acid (compound of formula III) are converted with a 2,3-diaminoquinoline derivative (compound of formula II) to give the compounds of formula I.

The synthesis of 4-methoxy-pyridin-2-carbaldehyde (compound of formula VI) is described for example in Ashlmori et al, Chem Pharm Bull 38, 2446-2458 (1990).

The synthesis of 3-(4-methoxypyridin-2-yl)propionic acid (compound of formula III) is described in the following examples or can be carried out as known to one of ordinary skill in the art.

Reaction Scheme 1:

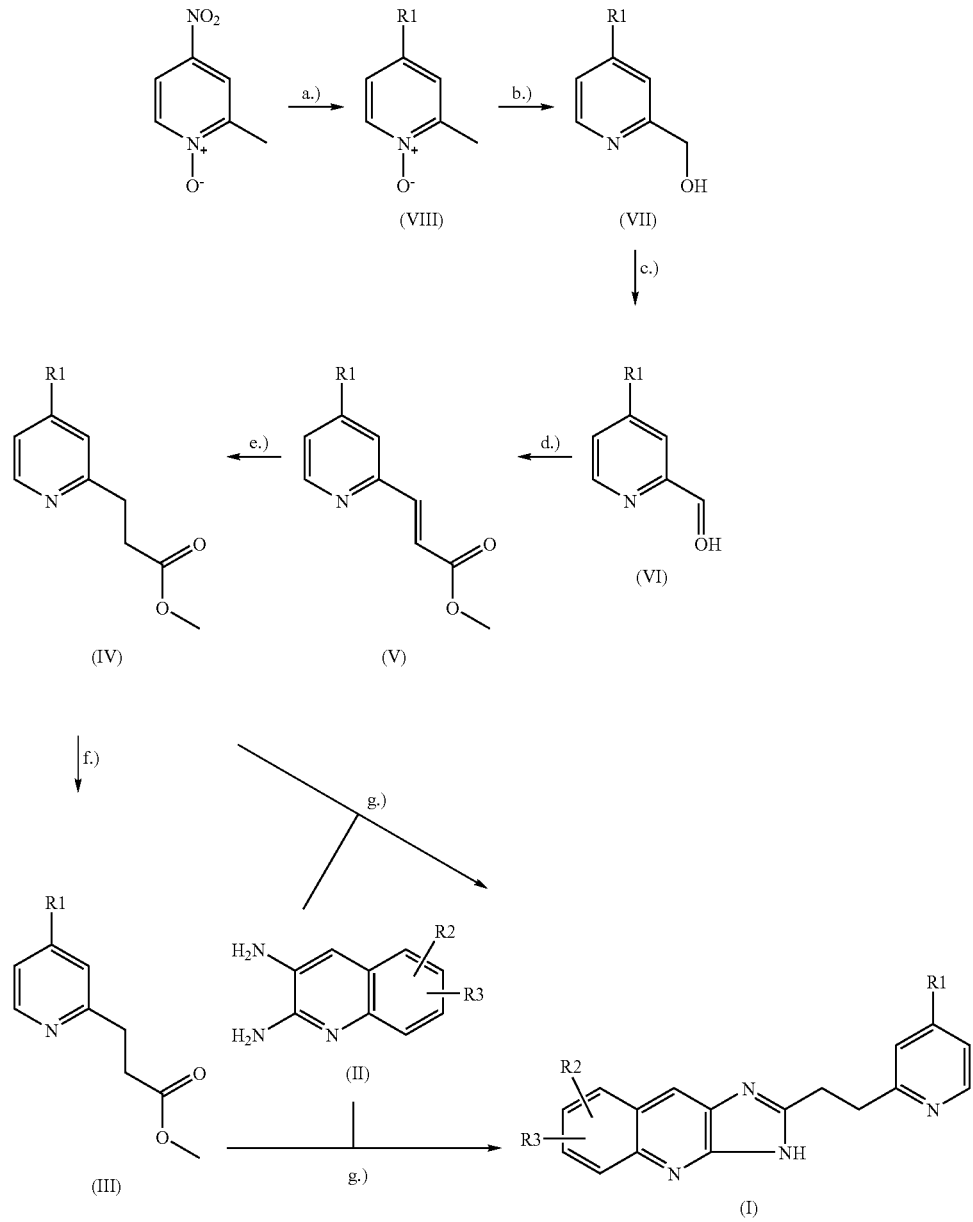

a.) NaR1/R1H b.) 1. Ac₂O 2. NaOH c.) 4-Methoxy-TEMPO/NaOCl
d.) Monomethyl malonate potassium salt/pyridine
e.) H₂/PdC (10%) f.) NaOH g.) Polyphosphoric acid The compounds of formula II are either known or can, for example, be prepared as described in the following examples according to reaction schemes 2 or 3.

In reaction schemes 2 and 3 the synthesis of compounds of formula II in which R2 and R3 independently of one another have the meanings indicated above is described exemplarily whereby each reaction step can be carried out as described by way of example in the following examples or in a manner known to the person skilled in the art or similarly or analogously thereto.

In a first reaction step the commercially available mucobromic acid is converted into the nitro containing dialdehyde compounds of formula XIII, which are transformed with commercially available or by art-known methods synthetically available aniline derivatives of formula XIV, in which R2 and R3 have the meanings given above, into the propenal derivatives of formula XII. These compounds of formula XII are converted by a ring closure reaction to the corresponding quinoline derivatives of formula XI. Subsequent N-oxide formation reaction gives the corresponding quinoline N-oxide derivatives of formula X which are subjected sequentially to a chlorination reaction, to a substitution reaction of the chlorine atom by an amino radical and to a reduction reaction of the nitro radical to furnish the desired 2,3-diaminoquinoline derivatives of formula II.

Reaction scheme 2:

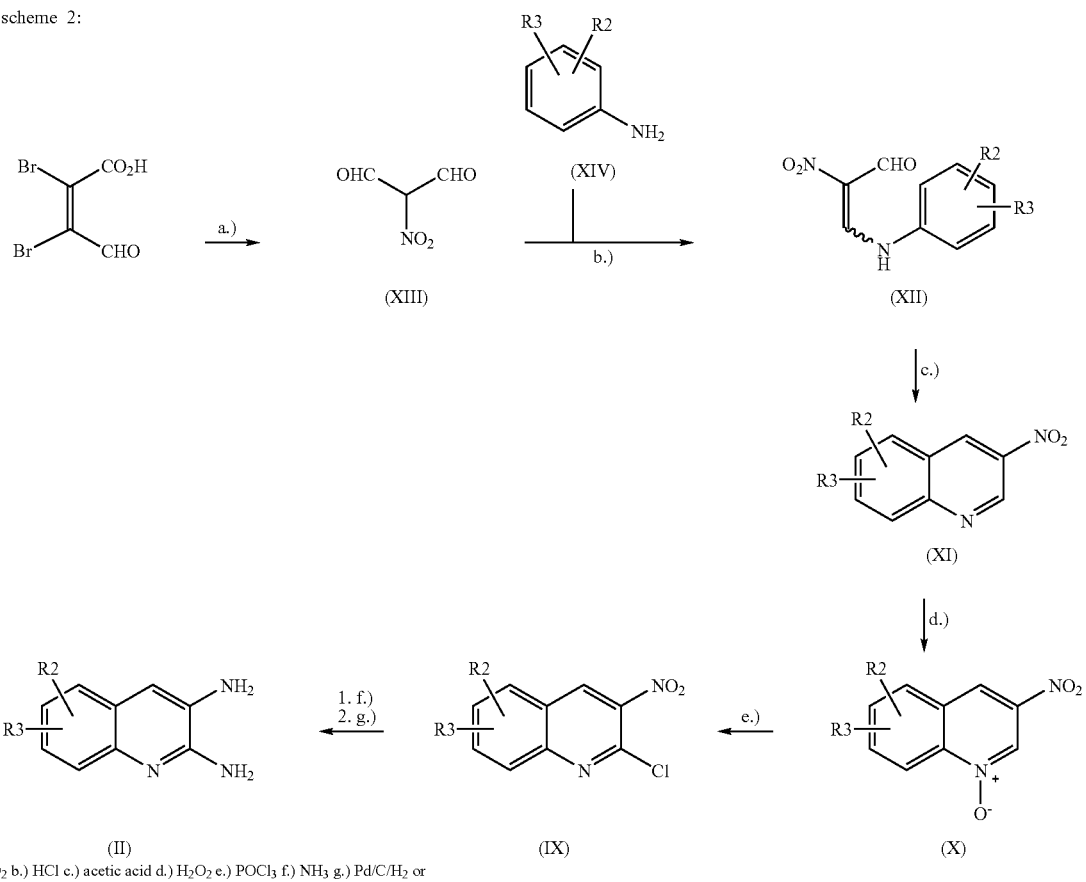

a.) NaNO$_2$ b.) HCl c.) acetic acid d.) H$_2$O$_2$ e.) POCl$_3$ f.) NH$_3$ g.) Pd/C/H$_2$ or FeCl$_3$/C/NH$_2$/NH$_2$ Alternatively, compounds of formula IX, in which R2 and R3 independently of one another have the meanings indicated above, can be also prepared according to reaction scheme 3. Commercially available or by art-known methods synthetically available quinoline N-oxide derivatives of formula XV, in which R2 and R3 have the meanings given above, are subjected sequentially to a nitration reaction and a chlorination reaction to give desired compounds of formula IX.

Reaction scheme 3:

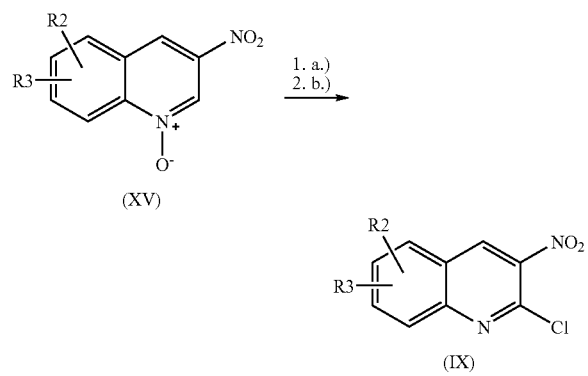

a.) AgNO$_3$ b.) POCl$_3$

The compounds of formula I can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

It is known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1991.

The substances according to the invention are isolated and pulled in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. Suitably, the conversions are carried out analogously to methods which are familiar per se to the person skilled in the art, for example, in the manner which is described in the following examples. As well, further compounds of formula I, of which the preparation is explicitly not described, can be prepared in an analogous way or in a way which is known by a person skilled in the art using customary preparation methods.

Having described the invention in detail and by reference to the embodiments thereof, the scope of the present invention is not limited only to those described embodiments. As it will apparent to persons skilled in the art, modifications, variations and adaptations to the described invention can be made on the base of the disclosure (e.g. the explicite, implicite or inherent disclosure) of the present invention without departing from the spirit and scope of this invention.

The compounds, which are mentioned in the examples as well as their salts, their N-oxides and the salts of the N-oxides are preferred compounds of the invention.

EXAMPLES

Final Products:

General Procedure for the Synthesis of Compounds 1 to 5:

1 mmol of 3-(4-methoxypyridin-2-yl)propylene acid (mentioned as compound F1) is added portionwise at 100-110° C. to a solution of 1 mmol of the appropriate 2,3-diaminoquinoline compound (mentioned as compound A1, compound B1, compound C1, compound D1 or compound E1) in 1.2 g of polyphosphoric acid. After stirring for 5-10 h at 120-165° C., the reaction mixture is cooled to room temperature, treated with 2 g of ice and neutralized with aqueous 5 N sodium hydroxide solution. The mixture is extracted three times each with 5 ml of dichloromethane. The organic phase are dried using magnesium sulfate, filtered and concentrated in vacuo. The residue is purified by chromatography on silica gel. The final compounds 1 to 5 are obtained as colourless solids.

1. 2-[2-(4-Methoxypyridin-2-yl)ethyl]-3H-imidazo[4,5-b]quinoline
   EF: $C_{18}H_{16}N_4O$
   MS: calc.: 304.3 fnd: 305.1 [MH$^+$]

2. 2-[2-(4-Methoxypyridin-2-yl)ethyl]-7-methyl-3H-imidazo[4,5-b]quinoline
   EF: $C_{13}H_{10}N_4O$
   MS: calc.: 318.4 fnd: 319.3 [MH$^+$]

3. 2-[2-(4-Methoxypyridin-2-yl)ethyl]-5-methyl-3H-imidazo[4,5-b]quinoline
   EF: $C_{19}H_{18}N_4O$
   MS: calc.: 318.4 fnd: 319.3 [MH$^+$]

4. 7-Methoxy-2-[2-(4-methoxypyridin-2-yl)ethyl]-3H-imidazo[4,5-b]quinoline
   EF: $C_{19}H_{18}N_4O_2$
   MS: calc.: 334.4 fnd: 335.3 [MH$^+$]

5. 7-Bromo-2-[2-(4-methoxypyridin-2-yl)ethyl]-3H-imidazo[4,5-b]quinoline
   EF: $C_{18}H_{15}BrN_4O$
   MS: calc.: 383.2 fnd: 385.2 [MH$^+$]

General Procedure for the Synthesis of Compounds 6 to 8:

1 mmol of 7-bromo-2-[2-(4-methoxypyridin-2-yl)ethyl]-3H-imidazo[4,5-b]quinoline (compound 5) and 1 mmol of the appropriate commercially available boronic acid known to the person skilled in the art are dissolved in 32 ml of dioxane. After addition of 3.6 ml of 2N aqueous sodium hydrogencarbonate solution and 50 mg of trans-dichlorobiscyclohexylphosphine)palladium, the reaction mixture is stirred under reflux over night. The resulting precipitate is filtered off, washed with dioxane and stirred in methanol. The solid is collected and dried to give the final compounds 6 to 8 as colourless crystals.

6. 7-(4-Hydroxyethylphenyl)-2-[2-(4-methoxypyridin-2-yl)ethyl]-3H-imidazo[4,5-b]quinoline
   EF: $C_{25}H_{22}N_4O_2$
   MS: calc.: 410.5 fnd: 411.4 [MH$^+$], 843.0 [2MNa$^+$]

7. 7-Benzofuran-2-yl-2-[2-(4-methoxypyridin-2-yl)ethyl]-3H-imidazo[4,5-b]quinoline
   EF: $C_{26}H_{20}N_4O_2$
   MS: calc.: 420.5 fnd: 421.3 [MH$^+$]

8. 7-(3,4-Dimethoxyphenyl)-2-[2-(4-methoxypyridin-2-yl)ethyl]-3H-imidazo[4,5-b]quinoline
   EF: $C_{26}H_{24}N_4O_3$
   MS: calc.: 440.5 fnd: 441.4 [MH$^+$]

Starting Compounds:

A1. 2.3-Diaminoquinoline

Compound A1 can be prepared according to K. S. Sharma et al. Synthesis 1981, 4, 316-318 and Ochlai. Kaneko et al. Chem. Pharm. Bull. 1959, 7, 267, 272, 273, 275 starting from commercially available quinoline N-oxide.

A2. 2,3-Diamino-8-methylquinoline 0.4 g of palladium on active carbon (5% Pd) is added to a solution of 1.1 g of 2-amino-3-nitro-8-methylquinoline (compound B1) in 50 ml of methanol/tetrahydrofurane 1:1 and the resulting suspension is hydrated for 1 h. The catalyst is filtered off and the filtrate is evaporated in vacuo. The residue is chromatographed on silica gel using dichloromethane/methanol 10:1 to give 0.79 g of the title compound as colourless solid.
   EF: $C_{10}H_{11}N_3$
   TLC: Rf=0.13 (dichloromethane/methanol 10:1)
   MS: calc.: 173.2 fnd: 174.3 [MH$^+$]

A3. 2,3-Diamino-6-methylquinoline 0.24 g of palladium on charcoal (10% Pd) is added to a solution of 1.32 g of 2-amino-3-nitro-6-methylquinoline (compound B2) in 100 ml of methanoltetrahydrofurane 1:1. After hydration for 1.5 h, the catalyst is filtered off and the filtrate is concentrated in vacuo. The residue is chomatographed on silica gel (dichloromethane/methanol 8:1). 1.02 g of the title compound are obtained as colourless solid.
   EF: $C_{10}H_{11}N_3$
   TLC: Rf=0.43 (dichloromethane/methanol 10:1)

A4. 2,3-Diamino-6-methoxyquinoline 10 mg of palladium on charcoal (10% Pd) are added to a solution of 0.64 g of 2-amino-3-nitro-6-methoxyquinoline (compound B3) in 40 ml of methanol/tetrahydrofurane 1:1. After hydration for 0.5 h, the catalyst is filtered off and the filtrate is concentrated in vacuo. 0.38 g of the title compound are obtained as light yellow solid.
EF: $C_{10}H_{11}NO_3$
TLC: Rf=0.36 (dichloromethane/methanol 6:1)

A5. 6-Bromo-2,3-aminoquinoline 76 mg of ferric trichloride and 125 mg of charcoal are added successively to a suspension of 0.5 g of 2-amino-6-bromo-3-nitroquinoline (compound B4) in 15 ml of methanol. Under reflux 0.4 ml of hydrazinium hydrate are added dropwise and reflux is continued for 3 h. After cooling to room temperature, the solids are filtered off and the filtrate is concentrated in vacuo. The residue is redissolved in 15 ml of dichloromethane/methanol 1:1 and extracted three times each with 15 ml of 0.25 M aqueous ethylene diamine tetraacetic acid (EDTA) solution. The organic layer is dried over magnesium sulfate, filtered and evaporated in vacuo to give 0.32 g of the title compound as brown residue.
EF: $C_9H_8N_3Br$
TLC: Rf=0.71 (dichloromethane/methanol 9:1)
MS: calc. 237.2 fnd: 238.3 [M⁺]

B1. 2-Amino-3-nitro-8-methylquinoline 1.6 g of 2-chloro-8-methyl-3-nitroquinoline (compound C1) is dissolved in 70 ml of ethanolic ammonia solution and stirred at 130° C. for 18 h in an autocave. After cooling to room temperature, the reaction mixture is concentrated in vacuo and the residue recrystallized from ethyl acetate. 1.2 g of the title compound are obtained as red solid.
EF: $C_{10}H_9N_3O_2$
TLC: Rf=0.55 (toluene/acetone 9:1)
MS: calc.: 203.2 fnd: 204.0 [MH⁺]

B2. 2-Amino-6-methyl-3-nitroquinoline 2.0 g of 2-chloro-6-methyl-3-nitroquinoline (compound C2) is dissolved in 100 ml of ethanolic ammonia solution and stirred at 130° C. for 6 h in an autoclave. After cooling to from temperature, the reaction mixture is concentrated in vacuo and the residue redissolved in 50 ml of ethyl acetate and extracted two times each with 50 ml of halfsaturated aqueous potassium carbonate solution. The organic phase is dried using magnesium sulfate, filtered and evaporated in vacuo. The residue is filtered over silica gel (dichloromethane). 1.5 g of the title compound are obtained as violet solid.
EF: $C_{10}H_9N_3O_2$
TLC: Rf=0.20 (dichloromethane)

B3. 2-Amino-6-methoxy-3-nitroquinoline 0.75 g of 2-chloro-6-methoxy-3-nitroquinoline (compound C3) are dissolved in 70 ml of ethanolic ammonia solution and stirred at 125° C. for 6 h in an autoclave. After cooling to room temperature, the reaction mixture is concentrated in vacuo and the residue redissolved in 30 ml of ethyl acetate and extracted two times each with 30 ml of halfsaturated aqueous potassium carbonate solution. The organic phase is dried using magnesium sulfate, filtered and evaporated in vacuo. The residue is filtered over silica gel (dichloromethane/methanol 8:2). 0.64 g of the title compound are obtained as violet sold.
EF: $C_{10}H_9N_3O_3$
TLC: Rf=0.15 (dichloromethane)

B4. 2-Amino-6-bromo-3-nitroquinoline 0.8 g of 2-chloro-6-bromo-3-nitroquinoline (compound C4) are dissolved in 12 ml of ethanolic ammonia solution and stirred at 120° C. for 2.5 h in an autoclave. Under cooling in an ice bath, 0.55 g of the title compound precipitate from the reaction mixture as red crystals.
EF: $C_9H_8N_3O_2Br$
TLC: Rf=0.55 (petroleum ether/ethyl acetate 7:3)
MS: calc.: 267.2 fnd: 268.2 [MH⁺]

C1. 2-Chloro-8-methyl-3-nitroquinoline

A suspension of 2.09 g of 3-nitro-8-methyl-quinoline-1-oxide (compound D1) in 15 ml of phosphorus oxychloride is stirred at 100° C. for 1 h. After cooling to room temperature, the reaction mixture is added to 40 ml of ice water and diluted with 50 ml of ethyl acetate. With the aid of solid potassium carbonate the pH value is adjusted to pH 8 and the mixture is extracted two times each with 30 ml of ethyl acetate. The combined organic phases are dried using magnesium sulfate, filtered and evaporated in vacuo. The residue is recrystallized from diethylether to give 1.3 g of the title compound as violet solid.
EF: $C_{10}H_7N_2O_2Cl$
TLC: Rf=0.75 (toluene/acetone 9:1)
MS: calc.: 222.6 fnd: 223.0 [MH⁺]

C2. 2-Chloro-6-methyl-3-nitroquinoline

A suspension of 0.43 g of 6-methyl-3-quinoline-1-oxide (compound D2) in 4 ml of phosphorus oxychloride is stirred at 100° C. for 16 min. After cooling to room temperature, the reaction mixture is added to 10 ml of ice water, diluted with 15 ml of dichloromethane and extracted with 20 ml of a halfsaturated aqueous sodium hydrogencarbonate solution. The organic layer is dried using magnesium sulfate, filtered and evaporated in vacuo. The residue is recrystallized from diethylether to give 0.44 g of the title compound as violet solid.
EF: $C_{10}H_7N_2O_2Cl$
TLC: Rf=0.72 (dichloromethane)
MS: calc.: 222.6 fnd: 223.2 [MH⁺]

C3. 2-Chloro-6-methoxy-3-nitroquinoline

A suspension of 8.0 g of 6-methoxy-3-nitroquinoline-1-oxide (compound D3) in 80 ml of phosphorus oxychloride is stirred at 100° C. for 30 min. After cooling to room temperature, the reaction mixture is added to 500 ml of ice water, diluted with 250 ml of dichloromethane and extracted three times each with 250 ml of a halfsaturated aqueous potassium carbonate solution. The organic layer is dried using magnesium sulfate, filtered and evaporated in vacuo. The residue is recrystallized from diethylether to give 5.6 g of the title compound as violet solid.
EF: $C_{10}H_7N_2O_3Cl$
TLC: Rf=0.75 (dichloromethane)

C4. 2-Bromo-2-chloro-3-nitroquinoline

A suspension of 1.0 g of 6-bromo-3-nitroquinoline-1-oxide (compound D4) in 7 ml of phosphorus oxychloride is stirred at 120° C. for 1.5 h. After cooling to room temperature, the reaction mixture is added to 15 ml of ice water, diluted with 20 ml of ethyl acetate and extracted with 20 ml of a halfsaturated aqueous sodium hydrogencarbonate solution. The organic layer is dried using magnesium sulfate, filtered and evaporated in vacuo. The residue is recrystallized from diethylether to give 0.82 g of the title compound as violet solid.
EF: $C_9H_4N_2O_2Br$
MS: calc.: 287.5 fnd: 288/286 [M⁺]

D1. 3-Nitro-8-methyl-quinoline-1-oxide 0.5 ml of benzoyl chloride are added dropwise to a suspension of 1.4 g of stirrer nitrate in 15 ml of dichloromethane. After 45 min stirring, the precipitate is filtered off and the filtrate is dropped to a solution of 1.0 g of 8-methylquinoline-oxide (compound E1) in 15 ml of dichloromethane at 0° C. The reaction mixture is refluxed for 1 h. After cooling to room temperature, the reaction mixture is diluted with 20 ml of dichloromethane and extracted two times each with 50 ml of halfsaturated aqueous sodium hydrogencarbonate solution. The organic layer is dried over magnesium sulfate, filtered and evaporated in vacuo. The residue is crystallized from acetonitrile to give 0.65 g of the title compound as yellow crystals.
EF: $C_{10}H_8N_2O_3$
TLC: Rf=0.55 (dichloromethane/methanol 95:5)
MS: calc.: 204.2 fnd: 205.0 [MH$^+$]

D2. 6-Methyl-3-nitroquinoline-1-oxide
A solution of 46 g of m-chloroperbenzoic acid in 19 ml of dichloromethane is added dropwise to a solution of 17.6 g of 6-methyl-3-nitroquinoline (compound E2) in 400 ml of dichloromethane. The reaction mixture is stirred for 70 h, diluted with 20 ml of dichloromethane and extracted two times each with 800 ml of halfsaturated aqueous sodium hydrogencarbonate solution. The organic layer is dried over magnesium sulfate, filtered and evaporated in vacuo. The residue is chromatographed on silica gel (dichloromethane/methanol 98:2). 8.25 g of the title compound are obtained as yellow crystals.
EF: $C_{10}H_8N_2O_4$
TLC: Rf=0.38 (dichloromethane/methanol 95:1)
MS: calc.: 204.2 fnd: 204.0 [MH$^+$]

D3. 6-Methoxy-3-nitroquinoline-1-oxide
19.2 g of benzoyl chloride are added dropwise to a suspension of 46.5 g of silver nitrate in 80 ml of dichloromethane at 15° C. The reaction mixture is stirred at room temperature for 0.5 h and at boiling temperature for 1 h. The precipitate is filtered off and the filtrate is dropped to a solution of 24.0 g of 6-methoxyquinoline-1-oxide (compound E3) in 80 ml of dichloromethane at 10° C. The reaction mixture is refluxed for 1.5 h. After cooling to room temperature, the reaction mixture is diluted with 200 ml of dichloromethane and extracted two times each with 200 ml of halfsaturated aqueous sodium hydrogencarbonate solution. The organic layer is dried over magnesium sulfate, filtered and evaporated in vacuo. The residue is recrystallized from ethyl acetate to give 8.2 g of the title compound as yellow crystals.
EF: $C_{10}H_8N_2O_4$
TLC: Rf=0.73 (ethyl acetate)
MS: calc.: 220.2 fnd: 220.0 [M1]

D4. 6-Bromo-3-nitroquinoline-1-oxide
22.5 ml of benzoyl chloride are added dropwise to a suspension of 66.0 g of silver nitrate in 300 ml of dichloromethane at 0° C. The reaction mixture is stirred at room temperature for 1 h. The precipitate is filtered off and the filtrate is dropped to a solution of 43.1 g of 6-bromoquinoline-1-oxide (compound E4) in 800 ml of dichloromethane at 10° C. The reaction mixture is refluxed for 2 h. After cooling to room temperature the reaction mixture is extracted two times each with 800 ml of halfsaturated aqueous sodium hydrogencarbonate solution. The organic layer is dried over magnesium sulfate, filtered and evaporated in vacuo. The residue is recrystallized from ethyl acetate to give 32.8 g of the title compound as yellow crystals.
EF: $C_9H_5N_2O_3Br$
TLC: Rf=0.76 (dichloromethane/methanol 98:2)
MS: calc.: 269.1 fnd: 268 [M$^+$]

E1. 8-Methyl-quinoline-1-oxide
A solution of 2.45 g of m-chloroperbenzoic acid in 15 ml of dichloromethane is added dropwise to a solution of 1 g of commercially available 8-methylquinoline in 15 ml of dichloromethane. The reaction mixture is stirred over night diluted with 30 ml of dichloremethane and extracted two times each with 50 ml of halfsaturated aqueous sodium hydrogencarbonate solution. The organic layer is dried over magnesium sulfate, filtered and evaporated in vacuo. The residue is chromatographed on silica gel (dichloromethane/methanol 98:2). 1 g of the title compound are obtained as colourless solid.
EF: $C_{10}H_9NO$
TLC Rf=0.38 (dichloromethane/methanol 95:5)
MS: calc.: 159.2 fnd: 160.1 [MH$^+$]

E2. 6-Methyl-3-nitroquinoline
The title compound is prepared according to Morley, Simpson; J. Chem. Soc. 1948, 2024, 2026.

E3. 6-Methoxyquinoline-1-oxide
The title compound is commercially available.

E4. 6-Bromoquinoline-1-oxide
The title compound is prepared according to Hamans; Nagayoshi Chem. Pharm. Bull. 1966, 14, 319, 321, 322; Ochlai; Okamoto; Yakugatu Zasshi 1948, 68, 88; Chem. Abstr., 1953, 8073.

F1. 3-(4-Methoxypyridin-2-yl)propionic acid
41.95 g of methyl 3-(4-methoxypyridin-2-yl)propionate (compound F2) are dissolved in 700 ml of tetrahydrofuran, and 217 ml of 1N sodium hydroxide solution are added. The mixture is stirred at RT until no more starting material is detectable (TLC). The mixture is neutralized using 217 ml of 1N hydrochloric acid solution, evaporated to dryness using a rotary evaporator and dried under high vacuum. The colorless residue is ground and extracted four times with dichloromethane/methanol (9:1). The combined extracts are evaporated to dryness. This gives 332 g of the title compound as a colorless powder of m.p. 131-132° C. The mass spectrum shows the molecular peak MH$^+$ at 182 Da F2. Methyl-3-(4-methoxypyridin-2-yl)propionate
43.1 g of methyl 3-(4-methoxypyridin-2-yl)acrylate (starting material F3) in 600 ml of methanol are hydrogenated over 3.0 g of Pd/C (10%) until the starling material has disappeared (TLC). The catalyst is filtered off, and the mixture is then concentrated and dried under high vacuum. This gives 41.95 g of the title compound as a light-yellow oil. The mass spectrum shows the molecular peak MH$^+$ at 196 Da.

F3. Methyl 3-(4-methoxypyridin-2-yl)acrylate
A mixture of 45 g of 4-methoxypyridine-2-carbaldehyde (Ashimori at al., Chem. Pharm. Bull. 38, 2446-2458 (1990)), 75.80 g of pyridine hydrochloride, 102.45 g of monomethyl malonate potassium salt and 4.1 ml of piperidine in 700 ml of pyridine are slowly heated, with stirring, to 120° C. When the evolution of gas starts, the heating source is temporarily removed to stop the reaction from becoming too violent. Once the reaction has subsided, the mixture is stirred at 120° C. for a further 2.5 h, and the pyridine is then distilled off under reduced pressure. The residue is partitioned between ethyl acetate/water and the organic phase is washed with water and dried. The residue obtained after concentration is chromatographed on a silica gel column using ethyl acetate/petroleum ether 2:1. This initially gives 43.2 g of the true compound as a yellow oil which crystallizes on standing and then shows a m.p. of 80-82° C. The mass spectrum shows the molecular peak MH$^+$ at 194 Da.

COMMERCIAL APPLICABILITY

The compounds according to the invention have valuable pharmacological properties which make them commercially utilizable. They are selective inhibitors of the enzyme inducible nitric oxide synthase. Nitric oxide synthases (NO-syntases, NOSs) are enzymes that generate NO and citrulline from the amino acid arginine. In certain pathophysiological situations such as arginine depletion or tetrahydrobiopterin depletion the generation of $O_2^-$ from NO-synthases instead or together with NO has been reported. NO is long known as a signalling molecule in most living organisms including mammals and humans. The most prominent action of NO is it's smooth muscle relaxing activity, which is caused on the molecular level by the activation of soluble guanylate cyclase. In the last years a lot of other enzymes have been shown to be regulated by NO or reaction products of NO.

There exist three isoforms of NO-synthases which fall into two classes and differ in their physiologic functions and molecular properties. The first class, known as constitutive NO-synthases, comprises of the endothelial NO-synthase and the neuronal NO-synthase. Both isoenzymes are expressed constitutively in various cell types, but are most prominent in endothelial calls of blood vassal walls (therefore called endothelial NO-synthase, eNOS or NOS-III) and in neuronal cells (therefore called neuronal NO-synthase, nNOS or NOS-I). Activation of these two enzymes is dependent on $Ca^{2+}$/Calmodulin which is generated by transient increases of the intracellular free $Ca^{2+}$ concentration. Activation of constitutive isoforms leads to transient bursts of nitric oxide resulting in nanomolar cellular or tissue NO concentrations. The endothelial isoform is involved in the physiologic regulation of blood pressure. NO generated by the neuronal isoform seems to have neurotransmitter function and the neuronal isoform is among other regulatory processes involved in memory function (long term potentiation).

In contrast to the constitutive isoforms the activation of inducible NO-synthase (INOS, NOS-II), the sole member of the second class, is performed by transcriptional activation of the INOS-promoter. Proinflammatory stimuli lead to transcription of the gene for inducible NO-synthase, which is catalytically active without increases in the intracellular $Ca^{2+}$-concentration. Due to the long half live of the inducible NO-synthase and the unregulated activity of the enzyme, high micromolar concentrations of NO are generated over longer time periods. These high NO-concentrations alone or in cooperation with other reactive radicals such as $O_2^-$ are cytotoxic. Therefore, in situations of microbial infections, INOS is involved in cell killing by macrophages and other immune cells during early nonspecific immune responses.

There are a number of pathophysiological situations which among others are characterized by the high expression of inducible NO-synthase and concomitant high NO or $O_2^-$ concentrations. It has been shown that these high NO concentrations alone or in combination with other radical spades lead to tissue and organ damage and are causally involved in these pathophysiologies. As inflammation is characterized by the expression of proinflammatory enzymes, including inducible NO-synthase, acute and chronical inflammatory processes are promising diseases for the therapeutic application of selective inhibitors of inducible NO-synthase. Other pathophysiologies with high NO-production from inducible NO-synthase are several forms of shock (septic, hemorrhagic and cytokine-induced).

It is clear that nonselective NO-synthase inhibitors will lead to cardiovascular and neuronal side effects due to concomitant inhibition of constitutive NO-synthase isoforms.

It has been shown in in-vivo animal models of septic shock that reduction of circulating plasma NO-levels by NO-scavenger or inhibition of inducible NO-synthase restores systemic blood pressure, reduces organ damage and increases survival (deAngelo Exp. Opin. Pharmacother. 19-29, 1999; Redl et al. Shock 8, Suppl. 51, 1997; Strand et al. Crit. Care Med. 26, 1490-1499, 1998). It has also been shown that increased NO production during septic shock contributes to cardiac depression and myocardial dysfunction (Sun et al. J. Mol. Cell Cardiol. 30, 989-997, 1998). Furthermore there are also reports showing reduced infarct size after occlusion of the left anterior coronary artery in the presence of NO-synthase inhibitors (Wang et al. Am. J. Hypertiens. 12, 174-182, 1999). Considerable inducible NO-synthase activity is found in human cardiomyopathy and myocarditis, supporting the hypothesis that NO accounts at least in part for the dilatation and impaired contractility in these pathophysiologies (de Belder et al. Br. Heart. J. 4, 426-430, 1995).

In animal models of acute or chronic inflammation, blockade of inducible NO-synthase by isoform-selective or nonselective inhibitors or genetic knock out improves therapeutic outcome. It is reported that experimental arthritis (Connor et al. Eur. J. Pharmacol. 273, 15-24, 1995) and osteoarthritis (Pelletier et al. Arthritis & Rheum. 41, 1275-1286, 1998), experimental inflammations of the gastro-intestinal tract (Zingarelli et al. Gut 45, 199-209, 1999). experimental glomerulonephritis (Narita et al. Lab. Invest. 72, 17-24, 1995), experimental diabetes (Corbett at al. PNAS 90, 8992-8995, 1993), LPS-induced experimental lung injury is reduced by inhibition of inducible NO-synthase or in INOS-knock out mice (Kristof et al. Am. J. Crit. Care. Med. 158, 1883-1889, 1998). A pathophysiological role of inducible NO-synthase derived NO or $O_2^-$ is also discussed in chronic inflammatory diseases such as asthma, bronchitis and COPD.

Furthermore, in models of neurodegenerative diseases of the CNS such as MPTP-induced parkinsonism, amyloid peptide induced Alzheimer's disease (Ishli et al., FASEB J. 14, 1485-1489, 2000), malonate induced Huntington's disease (Connop et al. Neuropharmacol. 35, 459-465, 1996), experimental menengitis (Korytko & Boje Neuropharmacol. 35, 231-237, 1996) and experimental encephalitis (Parkinson et al. J. Mol. Med. 75, 174-186, 1997) a causal participation of NO and inducible NO-synthase has been shown.

Increased INOS expression has been found in the brains of AIDS victims and it is reasonable to assume a role of INOS in AIDS related dementia (Bagasra et al. J. Neurovirol. 3 153-167, 1997).

Other studies implicated nitric oxide as a potential mediator of microglia dependent primary demyelination, a hallmark of multiple sklerosis (Parkinson et al. J. Mol. Med. 75, 174-186, 1997).

An inflammatory reaction with concomitant expression of inducible NO-synthase also takes place during cerebral ischemia and reperfusion (Iadecola et al. Stroke 27, 1373-1380, 1996). Resulting NO together with $O_2^-$ from infiltrating neutrophils is thought to be responsible for cellular and organ damage. Also, in models of traumatic brain injury (Mesenge et al. J. Neurotrauma 13, 209-214, 1996; Wada et al. Neurosurgery 43, 1427-1436, 1998) NO-synthase inhibitors have been show to posses protective properties. A regulatory role for inducible NO-synthase has been reported in various tumor cell lines (Tozer & Everett Clin Oncol. 9. 357-264, 1997).

On account of their inducible NO-synthase-inhibiting properties, the compounds according to the invention can be employed in human and veterinary medicine and therapeutics, where an excess of NO or $O_2^-$ due to increases in the activity of inducible NO-synthase is involved. They can be used without limitation for the treatment and prophylaxis of the following diseases:

Acute inflammatory diseases: Septic shock, sepsis, SIRS, hemorrhagic shock, shock states induced by cytokine therapy (IL-2, TNF), organ transplantation and transplant rejection, head trauma, acute lung injury, ARDS, inflammatory skin conditions such as sunburn, inflammatory eye conditions such as uveltis, glaucoma and conjunctivitis.

Chronic inflammatory diseases of peripheral organs and the CNS: gastrointestinal inflammatory diseases such as Crohn's disease, inflammatory bowel disease, ulcerative colitis, lung inflammatory diseases such as asthma and COPD, arthritic disorders such as rheumatoid arthritis, osteoarthritis and gouty arthritis, heart disorders such as cardiomyopathy and myocarditis, arterosklerosis, neurogenic inflammation, skin diseases such as psoriasis, dermatitis and eczema, diabetes, glomerulonephritis; dementias such as dementias of the Alzheimer's type, vascular dementia, dementia due to a general medical condition, such as AIDS-, Parkinson's diseases, Huntington's induced dementias, ALS, multiple sclerosis; necrotizing vasculitides such as polyarteritis nodosa, serum sickness, Wegener's granulomatosis, Kawasaki's syndrom; headaches such as migraine, chronic tension headaches, duster and vascular headaches, post-traumatic stress disorders; pain disorders such as neuropathic pain; myocardial and cerebral ischemia/reperfusion injury.

The compounds may also be useful in the treatment of cancers that express nitric oxide synthase.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to this invention for the production of pharmaceutical compositions having an INOS inhibitory activity.

The invention furthermore relates to pharmaceutical compositions for the treatment and/or prophylaxis of the illnesses mentioned, which contain one or more of the compounds according to the invention.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as ITS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permiasion promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient in addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for INOS inhibitors. Topical application forms (such as ointments) for the treatment of dermatoses thus contain the active compounds in a concentration of, for example, 0.1-99%. The dose for administration by inhalation is customarily between 0.1 and 10 mg per day. The customary does in the cans of systemic therapy (p.o.) is between 0.3 and 30 mg/kg per day, (i.v.) is between 0.3 and 30 mg/kg/h.

Biological Investigations

Measurement of Inducible NO-synthase Activity

The assay is performed in 96-well microliter F-plates (Greiner, Frickenhausen, FRG) in a total volume of 100 µl in the presence of 100 nM calmodulin, 226 µM $CaCl_2$, 477 µM $MgCl_2$, 5 µM flavin-adenine-dinucleotide (FAD), 5 µM flavin mononucleotide (FMN), 0.1 mM NADPH, 7 mM glutathione, 10 µM BH4 and 100 M HEPES pH 7.2. Arginine concentrations are 0.1 μM for enzyme inhibition experiments. 150000 dpm of [$^3$H]arginine are added to the assay mixture. Enzyme reaction is started by the addition of 4 μg of a crude cytosolic fraction containing human inducible NO-synthase and the reaction mixture is incubated for 45 to 60 min at 37° C. Enzyme reaction is stopped by adding 10 μl of 2M MES-buffer pH 5.0. 50 μl of the incubation mixture are transferred into a MADP N65 filtration microtiter plate (Millipore, Eschborn, FRG) containing already 50 μl of AG-50W-X8 cation exchange resin (Biorad, München, FRG). The resin in the Na loaded form is pre-equilibrated in water and 70 μl (corresponding to 50 μl dry beads) are pipetted under heavy stirring with a 8 channel pipette into the filtration plate. After pipetting 50 μl of the enzyme reaction mixture onto the filtration plates, the plates are placed on a filtration manifold (Porvair, Shepperton, UK) and the flow through is collected in Pico scintillation plates (Packard, Meriden, Conn.). The resin in the filtration plates is washed with 75 μl of water (1×50 μl and 1×25 μl) which is also collected in the same plate as the sample. The total flow through of 125 μl is mixed with 175 μl of Microscint-40 scintillation cocktail (Packard) and the scintillation plate is sealed with TopSeal P-foil (Packard). Scintillation plates are counted in a scintillation counter.

For the measurement of inducible NO-synthase-inhibiting potencies of compounds increasing concentrations of inhibitors were included into the incubation mixture. $IC_{50}$-values were calculated from the percent inhibition at given concentrations by nonlinear least square fitting.

The inhibitory values determined for the compounds according to the invention follow from the following table A, in which the compound numbers correspond to the example numbers.

TABLE A

Inhibition of INOS activity [measured as $-\log IC_{50}$ (mol/l)]

| compound | $-\log IC_{50}$ |
|---|---|
| 1 | 7.05 |
| 2 | 6.93 |
| 3 | 6.87 |
| 4 | 6.99 |
| 5 | 7.11 |
| 6 | 6.44 |

The invention claimed is:
1. A compound of formula I

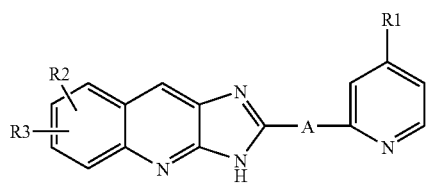

(I)

R1 is 1-4C-alkoxy;
A is 1-4C-alkylene;
R2 is hydrogen; halogen; 1-7C-alkyl; 1-4C-alkoxy; R21- and/or R22-substituted phenyl; or Het; in which
R21 is 1-4C-alkoxy; or hydroxy-1-4C-alkyl;
R22 is 1-4C-alkoxy;
Het is benzofuranyl; and
R3 is hydrogen; halogen; 1-4C-alkyl; or 1-4C-alkoxy;
or a salt thereof.

2. A compound of formula I according to claim 1 in which
R3 is hydrogen;
or a salt thereof.

3. A compound of formula I according to claim 1 in which
R1 is methoxy;
A is ethylene;
R2 is hydrogen; halogen; 1-4C-alkyl; 1-4C-alkoxy; R21- and/or R22-substituted phenyl; or Het; wherein
R21 is 1-4C-alkoxy;
R22 is 1-4C-alkoxy;
Het is benzofuranyl;
R3 is hydrogen;
or
R1 is methoxy;
A is ethylene;
R2 is hydrogen; halogen; 1-4C-alkyl; 1-4C-alkoxy; R21- substituted phenyl; or Het; wherein
R21 is hydroxy-1-4C-alkyl;
Het is benzofuranyl;
R3 is hydrogen;
or a salt thereof.

4. A compound of formula I according to claim 1 which is selected from the group consisting of
2-[2-(4-methoxypyridin-2-yl)ethyl]-3H-imidazo[4,5-b]quinoline,
2-[2-(4-methoxypyridin-2-yl)ethyl]-7-methyl-3H-imidazo[4,5-b]quinoline,
2-[2-(4-methoxypyridin-2-yl)ethyl]-5-methyl-3H-imidazo[4,5-b]quinoline,
7-methoxy-2-[2-(4-methoxypyridin-2-yl)ethyl]-3H-imidazo[4,5-b]quinoline,
7-bromo-2-[2-(4-methoxypyridin-2-yl)ethyl]-3H-imidazo[4,5-b]quinoline,
7-(4-hydroxymethylphenyl)-2-[2-(4-methoxypyridin-2-yl)ethyl]-3H-imidazol[4,5-b]quinoline,
7-benzofuran-2-yl-2-[2-(4-methoxypyridin-2-yl)ethyl]-3H-imidazo[4,5-b]quinoline,
7-(3,4-dimethoxyphenyl)-2-[2-(4-methoxypyridin-2-yl)ethyl]-3H-imidazo[4,5-b]quinoline,
and salts thereof.

5. A compound of formula I according to claim 1 in which R1 is methoxy and A is ethylene, or a salt thereof.

6. A pharmaceutical composition comprising one or more compounds of formula I according to claim 1, or a salt thereof, together with a pharmaceutically acceptable auxiliary and/or excipient.

* * * * *